United States Patent [19]

Walter, Jr. et al.

[11] 4,321,461
[45] Mar. 23, 1982

[54] FLOW RATE MONITOR AND TOTALIZER WITH COUNT DISPLAY

[75] Inventors: David E. Walter, Jr.; Max G. Kolmes, both of Milan, Tenn.

[73] Assignee: K/W/D Associates, Memphis, Tenn.

[21] Appl. No.: 141,644

[22] Filed: Apr. 18, 1980

[51] Int. Cl.³ .................... G06M 3/02; G08B 21/00; A16M 5/16

[52] U.S. Cl. .................... 235/92 FL; 128/214 E; 222/59; 235/92 V; 340/608; 340/609

[58] Field of Search .................... 340/606, 608, 609; 128/214 E, 204.23; 235/92 FL, 92 PC, 92 PE, 92 S, 92 V; 137/486, 487.5; 222/59

[56] References Cited

U.S. PATENT DOCUMENTS

| | | | |
|---|---|---|---|
| 3,163,176 | 12/1964 | Darling | 128/214 E X |
| 3,985,133 | 10/1976 | Jenkins et al. | 128/214 E X |
| 4,001,801 | 1/1977 | Moulet | 340/606 X |
| 4,018,362 | 4/1977 | Ubaud | 128/214 E X |
| 4,068,130 | 1/1978 | Malinowski | 340/630 X |
| 4,128,756 | 12/1978 | Nagano et al. | 235/92 SB |
| 4,205,238 | 5/1980 | Shim et al. | 235/92 FL X |

OTHER PUBLICATIONS

IBM Technical Disclosure Bulletin, vol. 12, No. 5, "Drop Detector" by E. Ellenwood, Oct. 1969, p. 693.

Primary Examiner—John W. Caldwell, Sr.
Assistant Examiner—Daniel Myer
Attorney, Agent, or Firm—Mason, Fenwick & Lawrence

[57] ABSTRACT

A flow rate monitor of solid particles or liquid drops and totalizing count display apparatus including a pulsed infrared light source and receiver forming a monitoring beam of high immunity to ambient light, transversely passing through a sensing chamber. A particular application is wherein the system is applied to the drop chamber of an intravenous set having electronic circuitry for pulsing the infrared light source and pulsing the sensing period of the monitoring beam receiver and producing a drop signal for each drop and a visible light flash for each sensed drop. Circuitry responds to the drop signals for maintaining a count of the number of drops and activating a visible numerical display indicating the drop count according to a selected numeric function, and an additional numeric display is provided adjacent the total count display indicating a selected checkpoint number. Alarm means are provided to produce visible and audible alarms signaling a No-Drop condition when an absence of drops occurs, as well as an alarm when a preselected count is reached. Alarm means are also provided to yield an audible alarm when a low battery voltage is reached.

18 Claims, 15 Drawing Figures

FLOW RATE MONITOR AND TOTALIZER WITH COUNT DISPLAY

BACKGROUND AND OBJECTS OF THE INVENTION

The present invention relates in general to liquid flow monitoring and flow control devices, and more particularly to a system for monitoring the drip rate in an intravenous infusion apparatus and to apparatus for setting the drip rate of such intravenous infusion apparatus.

The general purpose of the intravenous flow rate counter apparatus is to measure and display the rate and volume of the flow of liquids being infused into a patient intravenously, to sense the presence or absence of a liquid drop and to electronically convert this presence or absence into both audible and visual information to assist the medical personnel to adjust the intravenous infusion apparatus to match the infusion rate prescribed by the treating physician. It is a purpose of the system to also monitor the total volume of liquid infused into the patient intravenously by use of a digital display, to warn the patient and/or the medical personnel if a blockage of the flow of the liquid into the patient has occurred. It allows the medical personnel to monitor the operation of the intravenous infusion apparatus at a distance and in a darkened room, and advises medical personnel when a given amount of fluid has been infused so that additional fluid or medication can be added to the intravenous solution.

The usual medical procedure for gradual intravenous introduction of fluids into the human body, such as liquid nutrients and medication, makes use of an apparatus commonly referred to as an Intravenous Set, hereinafter generally referred to as an "IV". This IV set is comprised of a container of fluid, normally supported in an inverted position, a valve mechanism which allows the fluid to drip out of the container at a controlled rate into a drip chamber below the container and a tube leading from the bottom of the drip chamber. The tube has a needle at its end which is inserted into the vein of the patient, allowing the fluid to flow into the patient. The drip chamber serves a dual function; it allows a nurse or other medical personnel to observe the rate at which the fluid drips out of the bottle, and it serves as a reservoir for the fluid at the lower end of the chamber to insure that no air enters the main feeding tube leading to the patient.

While observation of the rate of flow via the drip chamber as a simple and effective way of controlling the amount of fluid fed into a patient over a period of time, its ultimate effectiveness requires that a relatively constant vigil be maintained over the drop flow. Otherwise, the patient's movements may cause the tube to become restricted, cutting off the flow of the fluids, the nurse may infuse an amount into the patient greater or at a faster rate than that called for by the physician's orders, or the supply of fluid into the bottle may become exhausted. It has been the general practice in hospitals to have nurses periodically monitor drop flow rates at each intravenous station, which is a tedious and time-consuming process, prone to error, with associated, possibly serious, consequences. It results in a substantial reduction of the available time of qualified medical personnel for other important duties. Typically, the nurse monitoring the drop flow rate will use a watch to time the number of drops flowing in an interval of one or more minutes, and will then mentally perform the mathematics necessary to convert the timed drop count to an appropriate rate, for example in cubic centimeters or milliliters per hour. If the calculated flow rate is substantially different from the prescribed rate, the nurse must manually adjust the tubing restriction device for a new rate, count drops again, and recalculate to measure the new rate. Obviously each of these described measurements and calculations and flow rate adjustments usually takes several minutes of time which, when multiplied by the number of stations being monitored and the number of times each station is monitored per day, can result in a substantial percentage of total personnel time available. Also, due to the pressure of other matters, the mental calculations performed by the nurse may not always prove to be reliable. This situation is compounded when the treating physician orders that additional medication be added to the IV fluid after a certain amount has been infused. Because of the importance of being able to accurately see or visually observe the drops of almost transparent liquid falling into the drip chamber to monitor the drip rate by this typical method, obviously the monitoring must be done in a lighted area.

An object of the present embodiment of this invention, therefore, is the provision of intravenous flow rate counter apparatus which optically monitors the drops of a liquid decending in the drip chamber of a conventional intravenous infusion set, by optically sensing the presence or absence of the liquid drop and electronically converting the data into both audible and visual information forms and visually informs the monitoring nurse of the existing drip rate, enabling the nurse or other monitoring personnel to promptly detect departures from the prescribed rate and adjust the device to the specified rate. This device does not influence or control either the drop rate or the volume of the liquid being administered to the patient, as these always remain strictly under the manual control of the nurse or other supervising personnel. An optical sensing head and its associated electronic circuitry is attached to and secured to any of the drip chambers of the standard types presently available, and is connected via a flexible electrical multiconductor cord to a battery and audible alarm box, which also includes electronic sensing circuitry for detection of No-Drop conditions. A display unit connected to this optical sensing head and battery and audible alarm box contains two displays of 4-digits each, one displaying the infused volume number in milliliters (ml) and the other the Check Point Volume in milliliters, and additionally includes a visual alarm and an audible alarm of different tone and pitch from that of the previously mentioned battery and alarm box, and also includes associated switches for digit setting and alarm resetting.

The Total-Volume Infused numerical display permits the nurse to see instantly how much IV solution has been given to the patient, and the Check Point Volume display is set to the total volume prescribed by the physician's orders, so that when the volume has been infused, both the audible alarm sounds and a light begins flashing advising the nurse that it is the correct time to add additional medication.

The optical sensing head unit includes a light emitting diode (LED) or similar small light emitter which causes a light, for example a small red light, to flash each time a drop falls, thereby permitting the nurse to observe from the door of the patient's from the flashing light and thus see that the IV appears to be operating, and by observing the constantly changing numbers on the digital display for infused volume, the nurse is insured that the IV set is working at the proper rate. If blockage occurs, the No-Drop alarm signal is activated and additionally the flashing drop indicating light ceases to flash, instantly advising the nurse of this condition.

Other objects, advantages and capabilities of the present invention will become apparent from the following detailed description, taken in conjunction with the accompanying drawings illustrating a preferred embodiment of the invention.

BRIEF DESCRIPTION OF THE FIGURES

FIGS. 12A, 13B and 12C collectively are a schematic diagram of calculator control circuitry which may be used in the drop rate setting embodiment.

DETAILED DESCRIPTION OF A PREFERRED EMBODIMENT

Figures 1, 2, 3:
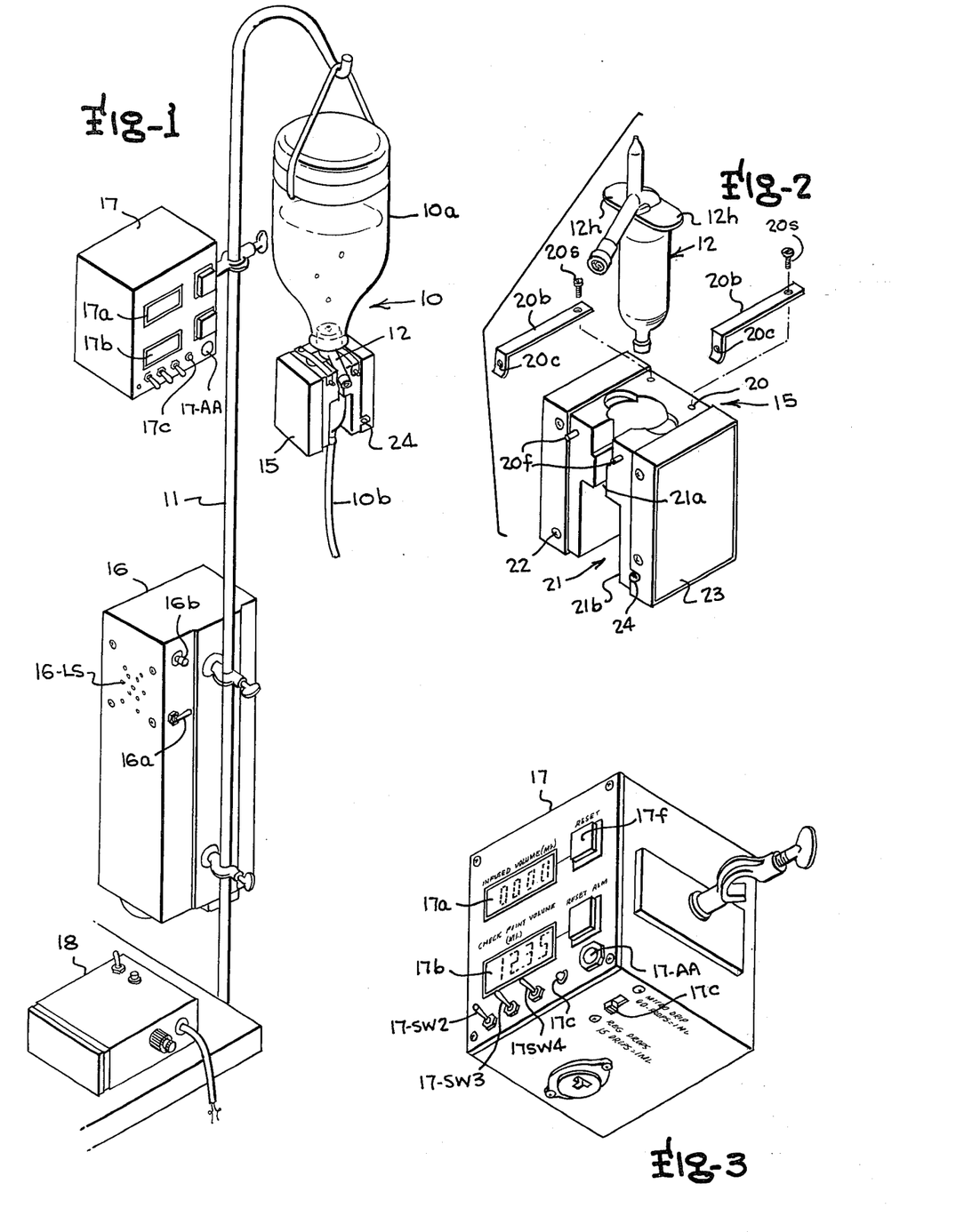
FIG. 1 is a somewhat diagrammatic perspective view of an intravenous flow monitoring system embodying the present invention.
FIG. 2 is an exploded perspective view of the optical sensing head unit.
FIG. 3 is a perspective view of the totalizer and display unit.

Referring to the drawings, wherein like reference characters designate corresponding parts throughout the several figures, there is illustrated in FIG. 1 in perspective and somewhat diagrammatic form the main components of the intravenous flow rate monitoring apparatus of the present invention. As illustrated in FIG. 1, the monitoring apparatus of the present invention is designed to be used with a standard intravenous infusion set such as the types manufactured by Abbott Laboratories, Travenol Laboratories and Cutler Laboratories, comprising the IV set generally indicated at 10 made up of a bottle of fluid 10a which is normally supported in inverted position, as shown, on a support stand 11, having an IV tube 10b extending from the mouth of the bottle with a drip chamber 12 of well-known construction at the bottle end of the tube having associated means for adjusting the desired drip rate and an ON-OFF clamp and the usual needle, not shown, at the end of the tube 10b which is inserted into the vein of the patient. The apparatus of the present invention includes an optical sensing head unit 15 which forms a surround about the drip chamber 12 and optically monitors the drops of liquid descending in the drip chamber of the intravenous infusion apparatus, a battery and alarm box 16 and a totalizer and display unit 17, together with certain optional auxiliary components as later described. The optical sensing head unit 15 optically senses the presence or absence of a liquid drop descending through the drip chamber 12 and electronically converts this data into visual information at the display unit 17 to better assist the nurse or other authorized personnel in adjusting the intravenous infusion set to the drip rate as described by the physician, as well as monitor at any time, the total volume infused into the patient. The optical sensing head 15 and its associated electronic circuitry is attached to the drip chamber 12 which it is to monitor, and is connected by way of a flexible electrical multiconductor cord to the battery and alarm box 16, which in the present invention also has electronic sensing circuitry for detection of No-Drop conditions. This unit is, in turn, connected to the display unit 17, which contains two displays 17a and 17b of 4-digits each, for example of the Liquid Crystal type, and includes additionally a visual alarm, indicated at 17c and an audible alarm of different tone and pitch from that of the battery and alarm box 16. The display unit 17 additionally incorporates a slide switch 17d, located on the bottom of the case, to enable selection of the division ratio of incoming pulses from the optical sensing head unit analogous to the liquid drops descending through the drip chamber 12. Division ratios of 60-drops to one ml or 15-drops to one ml are available for selection by the supervising nurse or personnel for the types of drop chamber utilized in this illustration. Other drop division ratios can be provided depending on the particular parameters of the drop chambers of the various manufacturers of this type of device.

The above generally described system is a battery operated set, in a preferred illustrative embodiment, capable of running at least seven days continuously from one battery charge, thus enabling it to be readily and conveniently moved from one location in the hospital to another as desired. Preferably, a battery charger unit 18 is also provided which is basically a battery charger used only when the system is not in patient use, to recharge the batteries and render it in condition for another use after a suitable storage or non-use period. The absense of connection to alternating currents supply outlets during operation removes the possible problem of patient electrocution due to faulty equipment. The battery charging unit 18, however, connects to any conventional 110-volt alternating current outlet when the unit is in storage or non-use, enabling the battery in the battery alarm box 16 to be recharged. A battery alarm, as later described, is provided in the battery and alarm box unit 16 which produces audible beeps at double the normal alarm rate for a period of time before operational failure occurs due to low battery. It will be appreciated, alternatively, that the unit may be operated directly from conventional AC supply outlets by design of an appropriate voltage reducing power supply and deletion of the battery pack.

Figure 4:
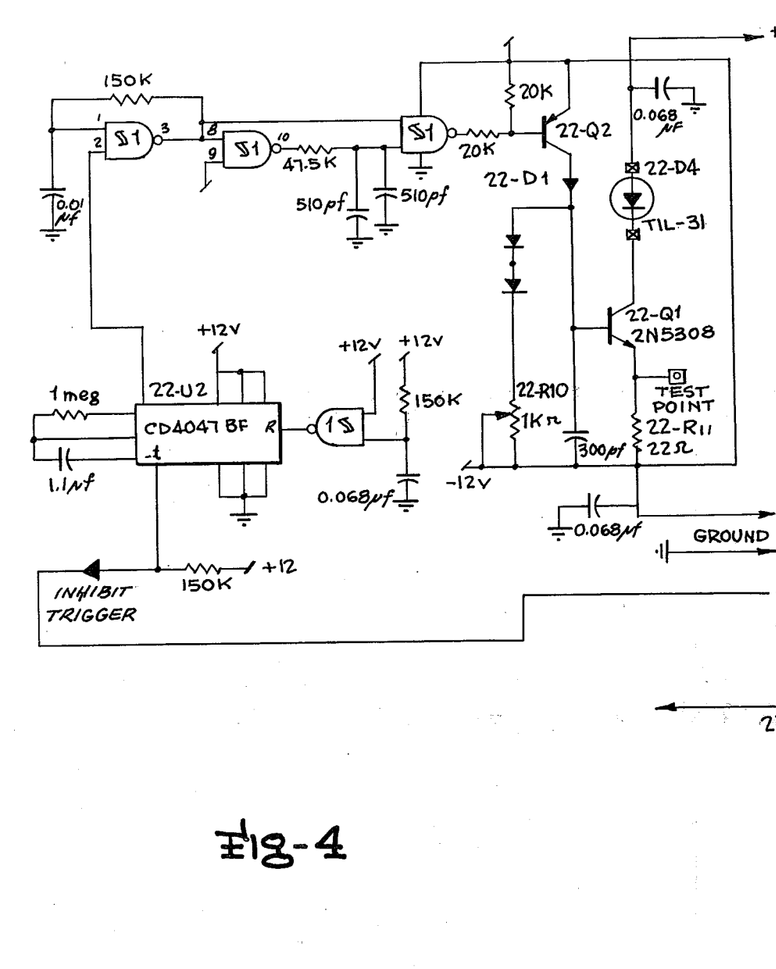
FIGS. 4 and 5 are schematic circuit diagrams of an infrared emitter circuit and a receiver circuit that may be used in the sensing head.
Figure 5:
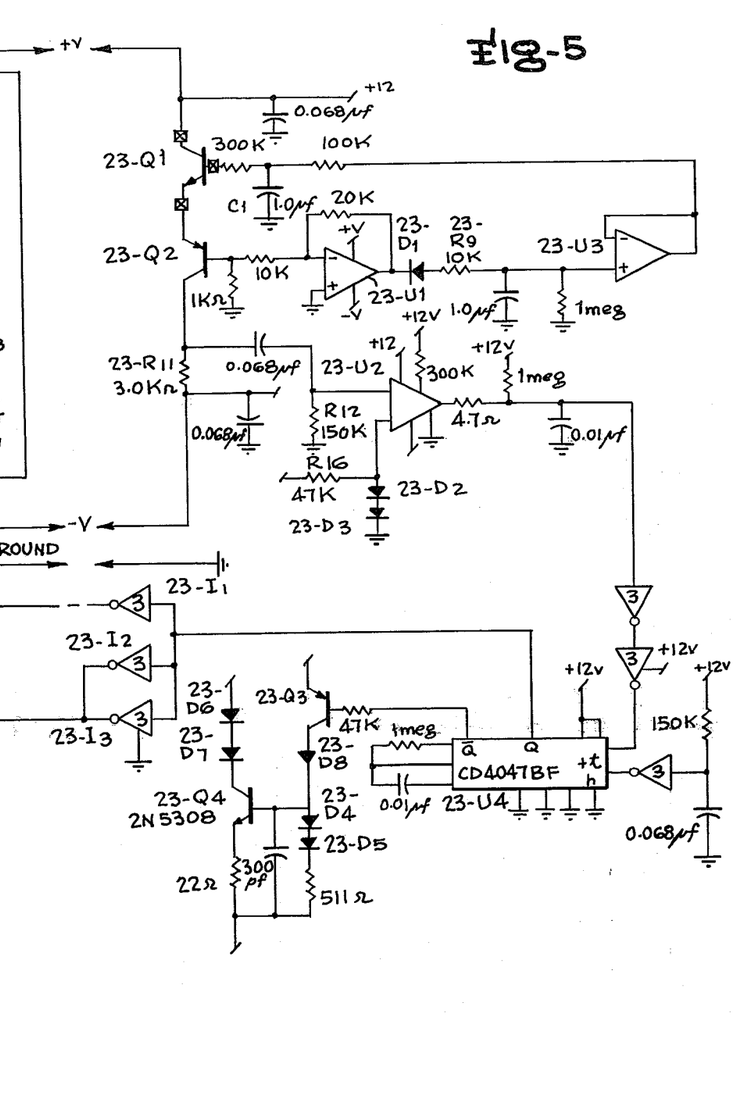

Referring more particularly to the structure and circuitry of the optical sensing head unit 15, as shown in FIGS. 2, 4 and 5, the sensing head unit 15 in the illustrated embodiment is in the general form of a cubic box, having a solid central core section 20 formed with a cavity 21 into which a drip chamber 12 of the IV infusion apparatus is received, flanked by two enclosed printed circuit board housing sections 22,23 fixed to the solid core section 20. The central core section 20 may, for example, be cast of a suitable resin material molded to form the flat, substantially square sides and top and bottom walls, with the cavity 21 drilled and reamed to appropriate diameter so that the IV drip chamber 12 inserts into the cavity with a minimum of clearance. The front access slot 21a is shaped so that the drop sensing head unit 15 may pass over the IV tubing to allow the IV drip chamber 12 to be inserted, and approximately the lower half of the front access slot is cutaway as indicated as 21b to provide an enlarged slot portion for allowing medical personnel access to the lower part of the IV drip chamber 12. This is desirable to faciliate application of thumb pressure to the IV drip chamber in order to prime the chamber with solution up to the level of the demarcation line provided by the manufacturer, in order to eliminate the possibility of air bubbles being generated by the falling drops of fluid.

The sensing head unit 15 may be conveniently removably suspended from the drip chamber 12 by two strap like hold down clamps 20b having a curved shape as shown in FIG. 2 and adapted to extend over the lateral wings 12h of the chamber 12. The clamps 20b may be spring steel straps assembled to the block 20 by screws 20s through holes in the rear portions of the clamps. Holes 20c in the front end portions of the clamps may be fitted over or removed from projections 20f on the block 20 to assemble the drip chamber to the block or remove it.

The entire surface of the cavity 21 confronting the drip chamber 12 is preferably blackened so as to minimize reflections, and a pair of aligned holes for receiving an infrared emitter and an infrared detector are drilled through the walls of the center core section along the desired horizontal line-of-sight or beam axis at right angles to the vertical axis of the drip chamber so that the center line of the monitoring beam of infrared light to be produced intersects the center line of the drip chamber at a 90° angle. In one example, the center line of the infrared (IR) emitter and receiver holes may be positioned about 0.250 inches below the tip of the metal tube forming the liquid drops in the drip chamber 12 of typical commercial construction, and with the IR emitter hole positioning the dome lens of the emitter close to the drip chamber and the IR receiver dome lens about 3/16 inches away from the drip chamber. This permits a wide latitude in operational variance to off vertical axis positioning of the container. Typically over 20 degrees variance from the off true vertical position of the container does not cause false operation.

An example of satisfactory IR light emitter circuitry which may be incorporated in the optical sensing head unit head 15 of the illustrative embodiments is illustrated in FIG. 4, wherein the IR emitting diode, which may be TIL-31, is indicated by the reference character 22-D4. The IR emitting diode 22-D4 is pulsed with a high current pulse provided by a constant current source having low duty cycle, for example by providing a circuit forming a free-running oscillator which triggers a narrow pulse monostable one-shot multivibrator on each oscillator cycle, which then causes a constant current source to pulse the IR emitting diode 22-D4. Typically, the diode 22-D4 is pulsed ON for 60 microseconds with a rate of 500 hertz (Hz). This method provides a high intensity IR light pulse, low heating of the emitting diode, and low total power consumption, the latter being a most important feature for battery operation. Also, the constant current source for driving the IR emitter permits uniform illumination for various power supply voltage levels. Included in the circuit is a trim potentiometer 22-R10 included in the constant current circuit for adjustment compensation for variations between the IR emitting 22-D4 and the companion lightreceiver transistor designed to receive and respond to the IR light beam.

Drop sensing is achieved by electrically sensing the change of light occurring during momentary interruption of the IR light beam. The IR light transmitted by the emitter diode 22-D4 is detected by a spectrally matched phototransistor, such as the phototransistor 23-Q1 in the IR receiving circuit of FIG. 5. As illustrated in FIG. 5, the phototransistor 23-Q1 drives a modified common base configuration transistor 23-Q2 that provides a low impedance to the phototransistor 23-Q1, and is connected to a circuit formed of Operational Amplifiers 23-U1 and 23-U3 as shown providing stabilization feedback and the necessary gain and smoothing for the stabilization feedback. The drop-analog pulse indicating change of light in the IR light beam signifying passage of a drop through the beam path is developed across the collector load resistor 23-R11 of transistor 23-Q2 and is sensed by the voltage comparator formed of Operational Amplifier 23-U2. Whenever these pulses exceed a set threshold level for about 10 milliseconds, a monostable one-shot multivibrator, formed by integrated circuit 23-U4, is triggered for a period of about 45 milliseconds, once and only once for each drop sensed. The monostable pulse thus produced is the electrical analog signal of a drop that is transmitted to the volume totalizing circuitry and other utilization circuitry of the system as later described.

An inhibit signal is also provided by the monostable one-shot multivibrator 23-U4 which is applied through inverter 23-I1, to the one-shot multivibrator 22-U2 of the FIG. 4 circuit, to trigger the one-shot multivibrator 22-U2 and reduce power consumption during a predetermined portion of the period of time elapsing between drops and thereby further reduce power consumption.

A significant feature of the optical sensing head unit 15 is the provision of highly visible LED 24 exosed at the front of the sensing head unit which flashes each time a drop interrupts the IR light path in the sensing head. This, in the particular example illustrated in FIG. 5, comprises a pair of LED's 23-D6 and 23-D7 pulsed by a constant current source for the 45 millisecond duration of the monostable pulse produced by the one-shot multivibrator 23-U4, and, by use of the constant current drive, allows stable light emission as the battery decays. The circuitry of FIG. 5 provides enhancement of immunity of the system to ambient light variations, by virtue of the provision of DC coupled negative feedback directly to the base of the phototransistor 23-Q1 to maintain specific gain conditions on the phototransistor, and by reason of sufficient integration on the negative feedback circuit to avoid overshooting and hunting, and separation of the integration and gain of the feedback circuit by two amplifiers.

The battery and alarm box unit 16 is connected to the optical sensing head 15 by a multiple conductor cable and houses batteries for energizing the system, such as a pair of gel-cells with a nominal potential of 12-volts each, together with current limiting resistors for all power feeds, a battery level monitor, circuitry for determining the presence or absence of drops, and circuitry for generation of audible alarms. Thus, in the event the drops cease to flow through the IV infusion system because of either internal or external blockage, or the fluid bottle runs dry, or the fluid flows in a constant stream, an audible alarm on the battery and alarm box unit 16 will be automatically activated after a suitable delay, for example 30 or 60 seconds, after the last drop falls. Preferably, the selection of the time-alarm-interval may be made by the supervising nurse or operating personnel by means of a switch 16a on the battery and alarm box 16. The illustrative 30 or 60 second delay after the last drop falls, is not a design restriction and can be varied depending on the medical judgment, as to how critical the medication lapse influences the intended treatment. Time(s) could be selected to be much shorter or longer and can be varied from zero seconds to infinity. The same "No-Drop alarm" is designed to also sound at double the normal rate if a low battery condition occurs, and will continue until the power switch is turned OFF or the unit is placed on charge. The "No-Drop alarm" is designed to automatically reset if the drops begin anew, so that, if the patient accidentally blocks the flow of fluid through the IV system, the sounding of the alarm may stimulate the patient to check the position of the IV tube or portion of the body in which the fluid is being administered, and if this corrects the interrupted drop flow, the system resumes normal operation. A Reset button, indicated at 16b is also provided on the battery and alarm box unit 16, which may be operated by the nurse or supervising personnel upon hearing the alarm and noting that the LED 24 providing the visible flashing system is not flashing, can reset the alarm so that it will terminate sounding for a selected delay period, while the nurse attempts to make necessary adjustments to resume proper intravenous flow, although the alarm will again sound if the flow does not resume by the end of the predetermined delay period.

Figure 6:
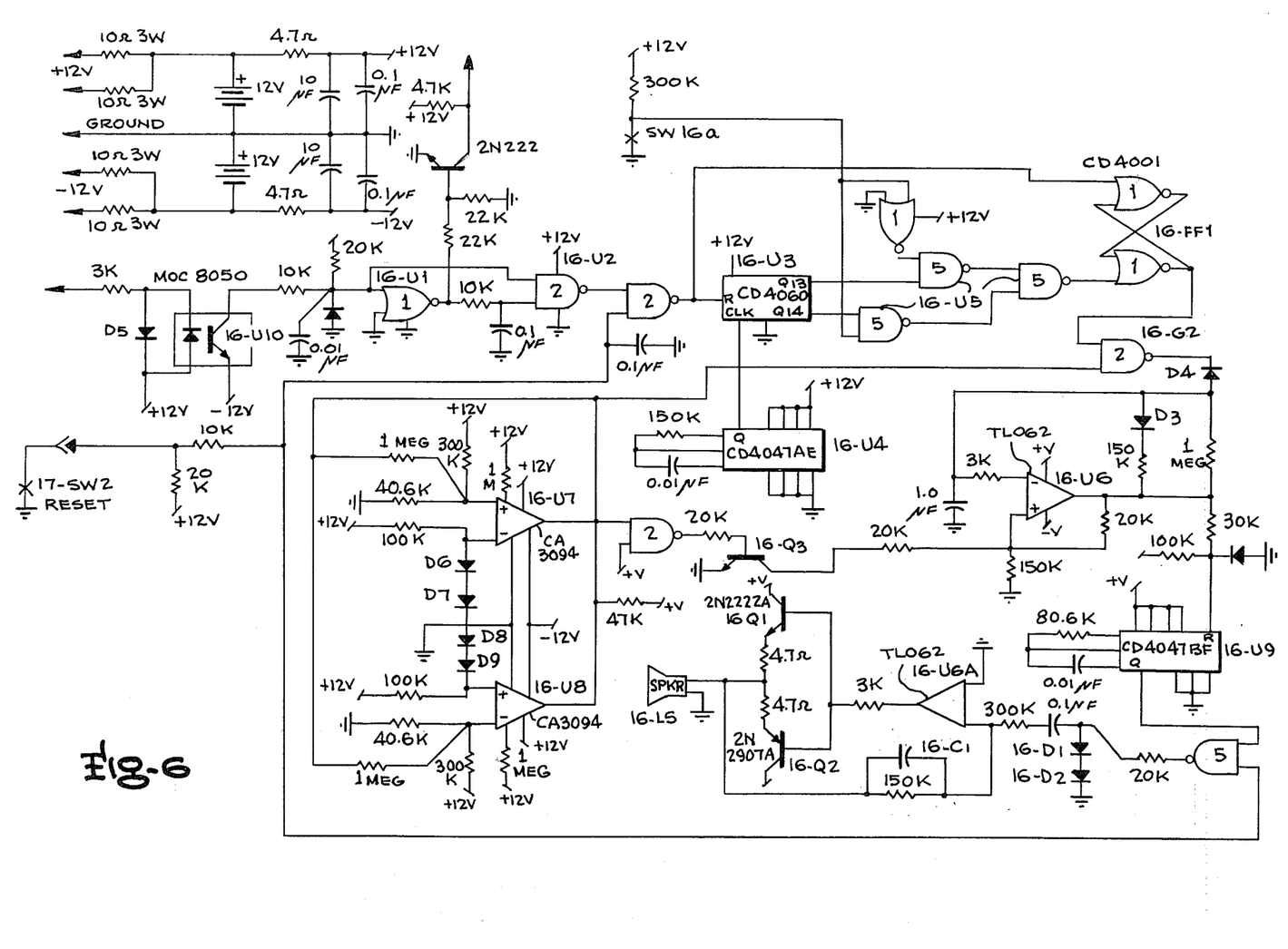
FIG. 6 is a schematic diagram of battery and alarm box circuitry and battery level monitoring circuit usable in the present invention.

Referring to FIG. 6, illustrating circuitry for the battery and alarm box unit 16 in schematic diagram form, the drop indicating pulses produced at the output of the one-shot multivibrator 23-U4 through the inverters 23-I2 and I3 connected to its output are supplied to the emitting side of an optical isolator, identified by the reference character 16-U10, comprising an emitter diode energized by the drop indicating pulses and a phototransistor activated thereby, which is for the purpose of providing high-level noise immunity from both ground loops and transients coupled into the cable. The pulses from this optical isolator 16-U10 trigger a monostable multivibrator, formed of interconnected NAND and NOR circuits 16-U1 and 16-U2, producing a pulse once, and only once, for each input pulse. This monostable circuit formed of 16-U1 and 16-U2 also has a small amount of integration for noise immunity. The pulse output from this one-shot monostable multivibrator circuit is coupled to the reset lead of a binary counter 16-U3 and causes the counter to reset to zero each time a drop falls as sensed by the optical sensing circuit. If the drops cease to fall, the clock pulses generated by clock pulse generator 16-U4 will cause counter 16-U3 to increment through internal divider stages Q13 and Q14 of the integrated circuit counter 16-U3. These outputs represent a delay of 30 seconds and 60 seconds respectively after the last drop passes the optical sensing circuit.

Selection of one or the other outputs representing the 30 second delay or 60 second delay is achieved by the switch 16A and gates 16-U5. When the selected delay signal appears, it sets a flip-flop 16-FF1, here formed of interconnected NOR gates, to enable the alarm circuitry to be described.

The alarm to be generated is a shaped square wave having a variable gating rate applied to the square wave oscillator enable control. As illustrated in FIG. 6, the alarm generator circuit may comprise an oscillator 16-U9 which generates a square wave at a frequency of, for example, 282 Hz, which is interrupted at a slow non-symmetrical rate for the No-Drop alarm, and at a faster rate for the low-battery alarm. Amplifier 16-U6 is the oscillator which provides the interruption rate, and is enabled by the logic gate 16-G2. This logic gate functions as the "OR" connection for the battery alarm enable signal and for the No-Drop alarm enable signal. Transistor 16-Q3 turns ON when the alarm is to signal a low-battery condition and causes the interruption rate to change.

An audio amplifier, formed of transistors 16-Q1 an 16-Q2 and Operational Amplifier 16-U6A along with associated passive components form a Class B audio amplifier drive for a conventional paper-cone loud speaker 16-LS. To assure a constant audio level as the battery level decays, the audio amplifier input signal is developed across two silicon diodes 16-D1 and 16-D2 which have a relatively constant voltage drop. Capacitor 16-C1 provides wave shaping.

Two voltage comparators indicated at 16-U7 and 16-U8 are connected with their outputs wired in an OR arrangement to form the low-battery level monitor, the comparator 16-U7 forming the positive battery monitor and 16-U8 the negative battery monitor. Whenever the battery level descends to about 8.4 volts, this level being selected by voltage divider resistors on the input arms of 16-U7 and 16-U8, the output of the respective comparator will switch into conduction and enable the alarm circuitry to produce the low voltage indicating audible alarm.

Figure 7:
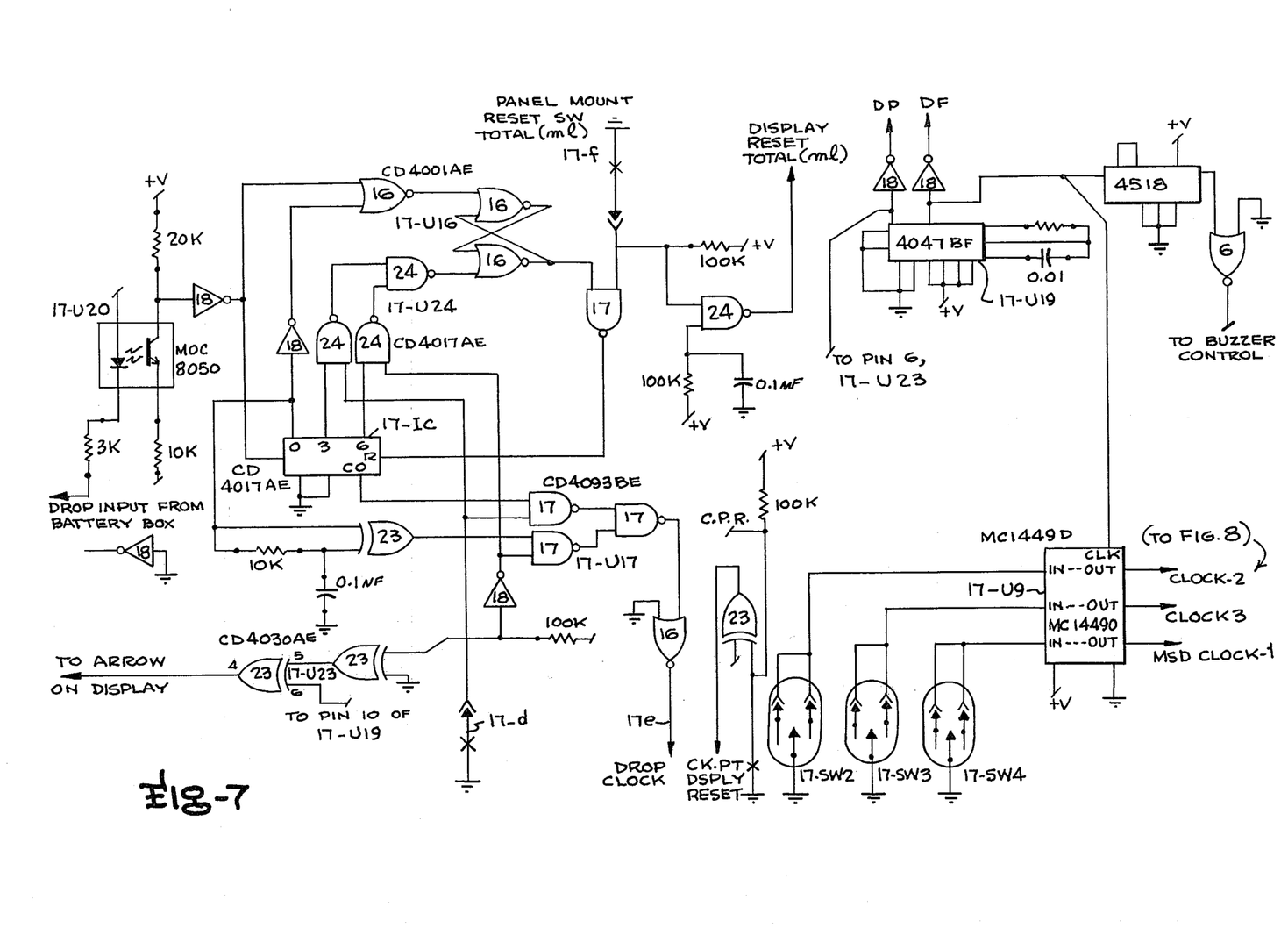
FIG. 7, 8 and 9 are schematic diagrams of circuitry making up the totalizer and display unit.
Figure 8:
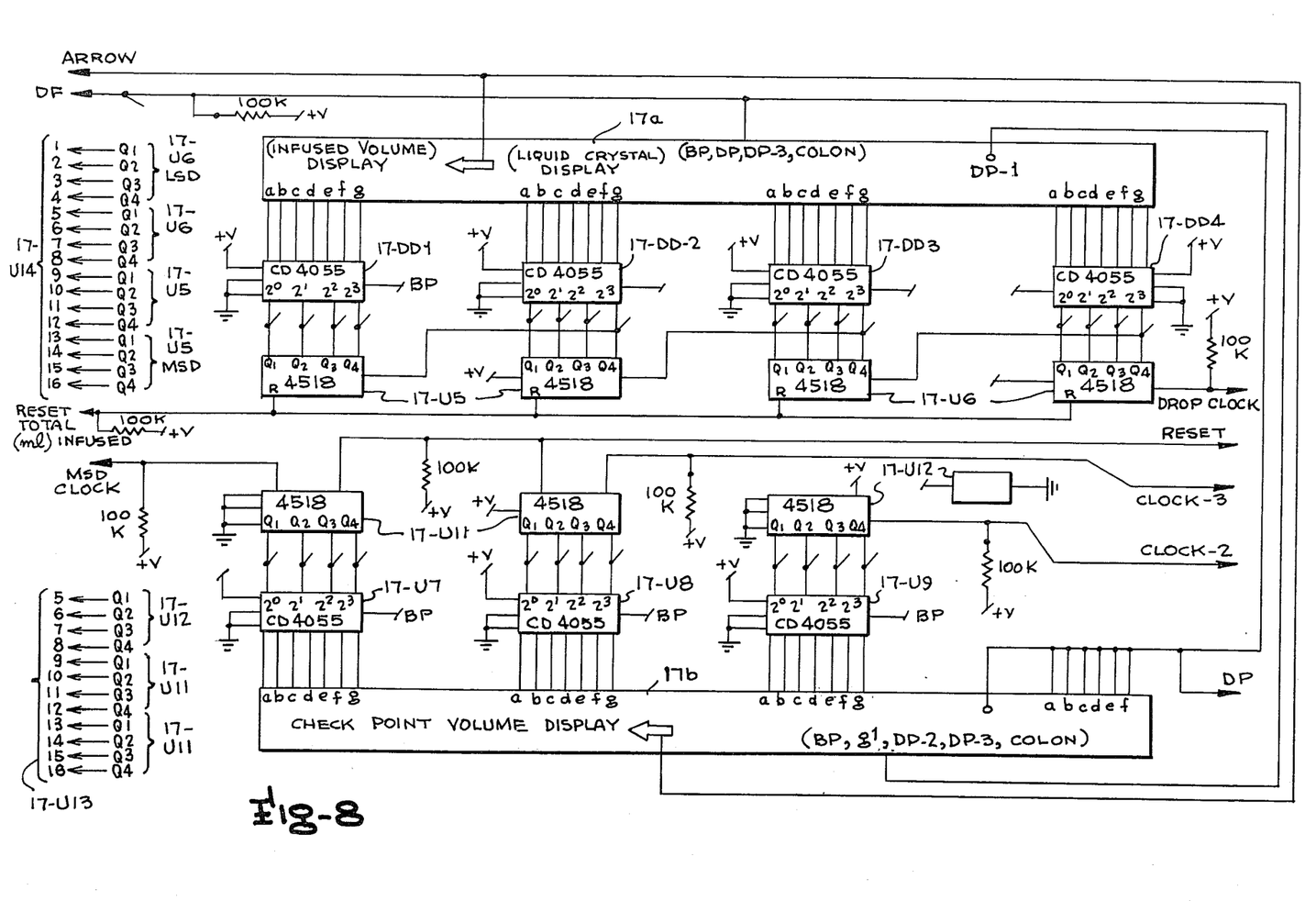
Figure 9:
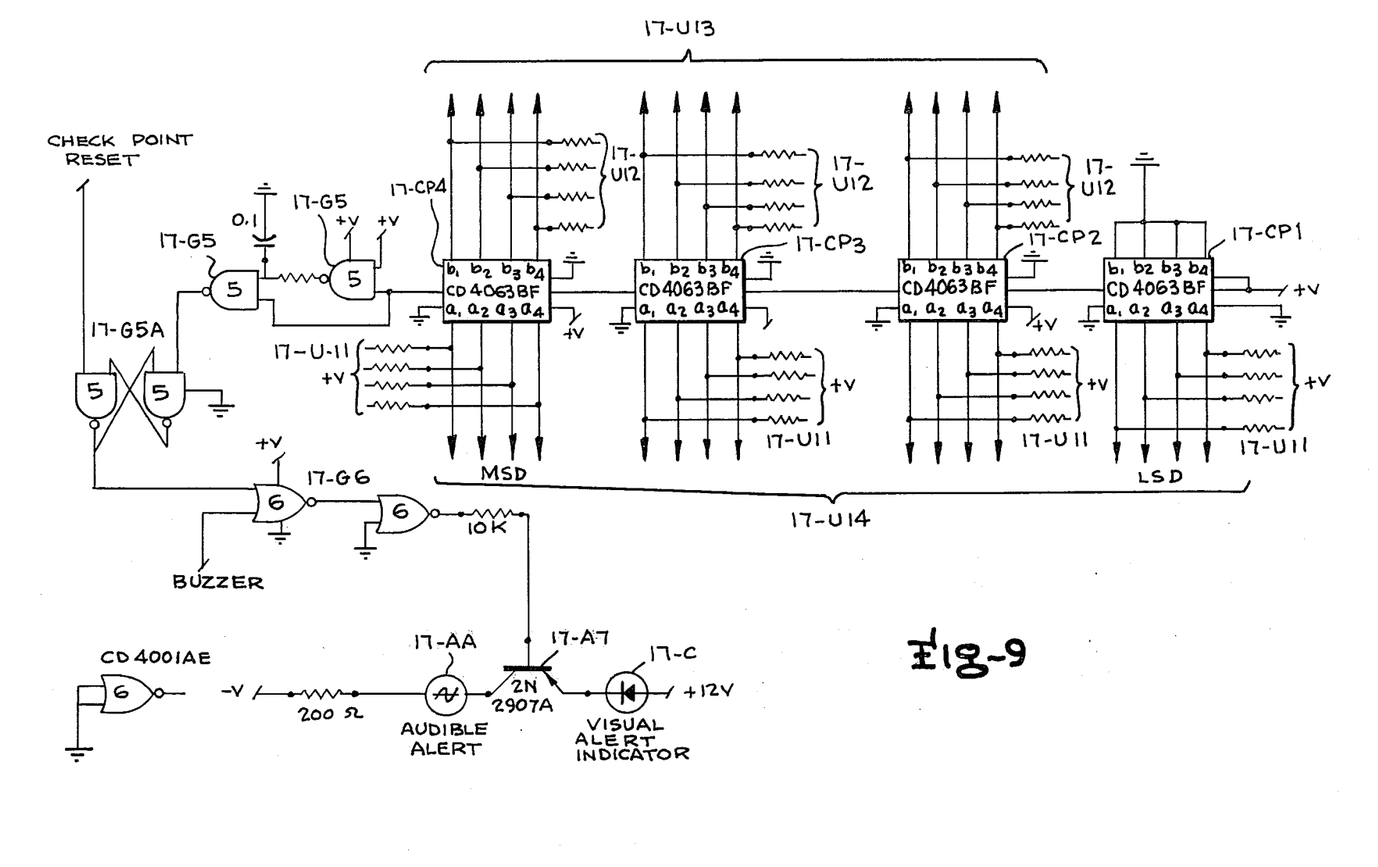

The volume totalization and display unit 17 providing the two visual displays 17a and 17b of the "Total Volume Infused" and the "Check Point Volume" is composed of three basic circuits. The first is an arithmetic section where division is accomplished, the second is a section where the checkpoint volume is set-up, and the third is the alarms. Referring to FIGS. 7, 8 and 9, disclosing schematic circuits which may be used in an illustrative embodiment of the volume totalization and display unit 17, there is provided an optical isolator, such as an MOC-8050, indicated by the reference character 17-U20, which receives drop indicating pulses from the output of the battery and alarm box unit 16, to provide high-level noise immunity as in the case of the input section of the battery and alarm box unit 16, and the consequent pulse output from the optical isolator is applied to integrated circuit 17-IC, which may be a CD 4017AE, which is a divider set for a division ratio by associated logic formed of the circuit elements 17-U23, 17-U16, 17-U24 and 17-U17. The division accomplished is determined by the slide switch 17d located on the bottom of the display unit 17 which selects a division constant to scale the drops/ml into just milliliters. The division constant varies according to the manufacturer of the drip mechanism being used. For example, for the Abbott Laboratories IV infusion system, wherein a "micro drip" and "regular drip" selection is available, the division constant for the regular drip is 3, with a double pulsing circuit that provides two counts for each group of three input pulses. For the "micro drop" mode, the division constant is 6 and double pulsing is not used. The end result is a pulse train from the output of the interconnected set of gate circuits 17-U16 which may be referred to as a "drop clock" pulse train that has a value of 0.1 ml/pulse, on the lead indicated at 17e in FIG. 7. These drop clock pulses drive 4 decades of cascaded binary coded decimal counters, indicated at 17-U5/U6, shown in FIG. 8, which in turn feed the respective display drivers 17-DD1, 17-DD2, 17-DD3 and 17-DD4. To distinguish operation of totalization of pulses from the micro drop chamber and from the regular drop chamber, a small arrow displayed in the top left-hand corner of the infused volume display is visible during operation for the regular drop. In production units this arrow may be replaced by an appropriate symbol display.

The checkpoint volume display 17b is set by manually pulsing the individual binary coded decimal counters 17-U11 and 17-U12, which in turn are connected to and drive the respective display drivers 17-U7, 17-U8 and 17-U9. The least significant digit, being 0.1 ml, is hard wired to read zero.

A comparison circuit, shown in FIG. 9, to test equality of Total Volume Infused against Check Point Volume is formed of four cascaded 4-bit comparators 17-CP1, 17-CP2, 17-CP3 and 17-CP4, with the final output driving a one-shot formed of interconnected NAND gates 17-G5, which in turn sets a flip-flop formed of NAND gates 17-G5A should a comparison match occur. The output from the flip-flop formed of gates 17-G5A is gated through NAND gates 17-G6 for the purpose of providing an interruption sound to the audible alert. This combination yields a sound that is distinctive and easily separated from the other audible alerts described previously, this audible alert being indicated in FIG. 9 at 17-AA and also as 17-AA in FIG. 3. A visual alert, indicated at 17c, is also provided as a LED connected in circuit with the audible alert 17-AA through the transistor 17-A7. A Reset is available by pressing the button to the right of the display 17b labeled "Check Point Volume" for resetting the display.

The digital displays, indicated schematically at 17a and 17b, are preferably four digit, 7 segments/digit, displays of the Liquid Crystal technology type. These displays have the advantage of low power consumption, large character size, increasing visibility with increasing ambient light, and display of special symbols, such as might be used to indicate different drop chambers.

Figures 10, 13:
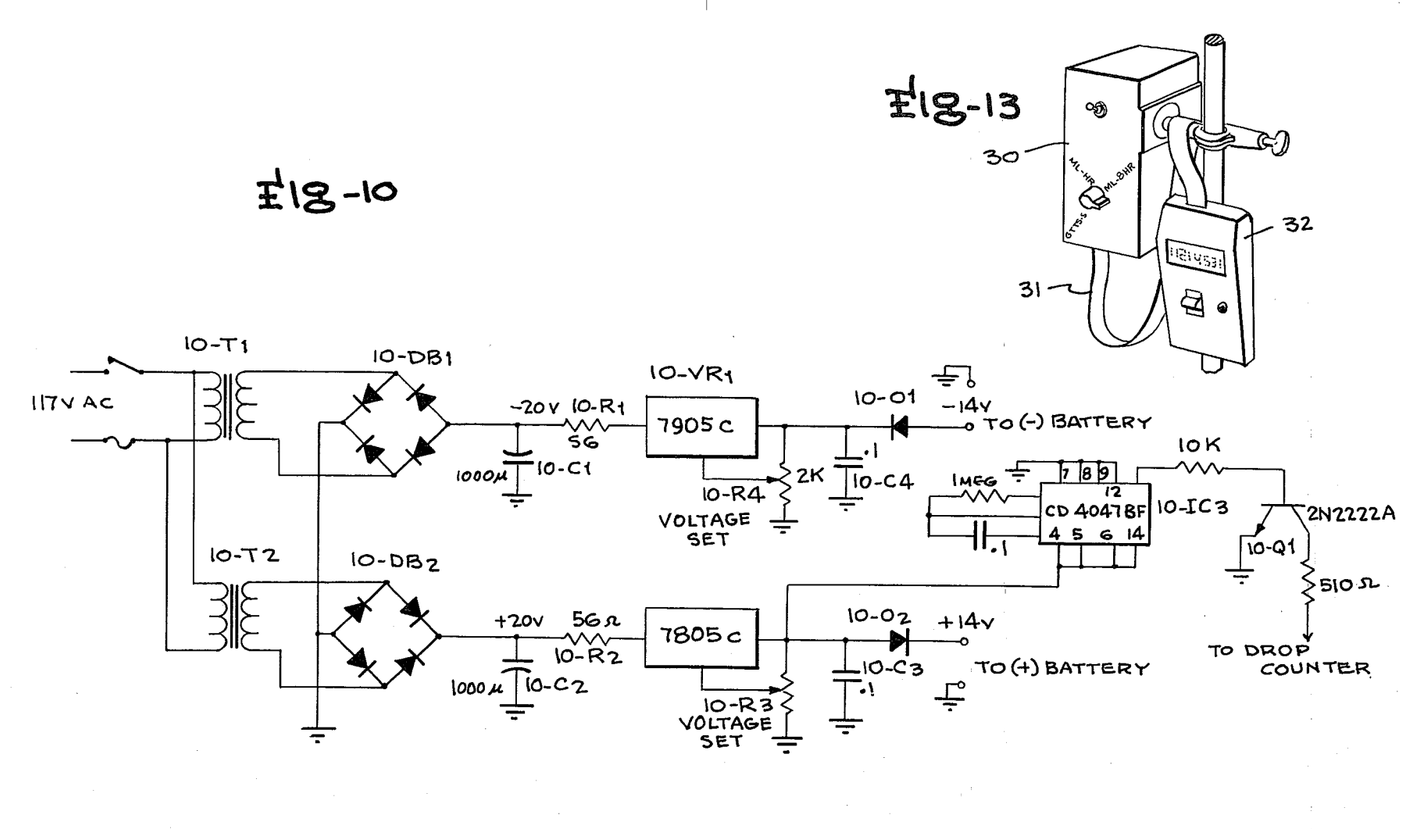
FIG. 10 is a schematic diagram of a battery charger circuit that may be used in the present invention.
FIG. 13 is a perspective view of an embodiment of the hand-held calculator and electronics package for the drop rate setting components.

In the commercial units designed to operate without being plugged into 110 volt supply outlets, a battery charger, as shown in FIG. 10, may be used, which may be a simple textbook style circuit having a constant voltage output with preset current limiting, and providing an independent charging circuit for each battery. Included in the battery charger package, in the illustrative embodiment, is a "drop pulse simulator circuit" that resets the alarm circuit in the battery box and prevents audible alarms during charging. As illustrated in FIG. 10, the battery charger may be provided with a transformer 10-T1 having a secondary diode bridge 10-DB1 and a capacitor 10-C1 forming an unregulated −20 volt power supply which is fed through a current limiting resistor 10-R1 to a monolithic voltage regulator, such as a Motorola 7905C, providing an output voltage, for example about −14 volts nominal, set by potentiometer 10-R4. This voltage may be adjusted with a 1.0K ohm resistive dummy load. The diode 10-D1 in the FIG. 10 circuit serves to protect the voltage regulator 10-VR1 from reverse voltage destruction, such as may occur when the AC power is OFF and the battery is connected. The capacitor 10-C3 serves to prevent the voltage regulator from oscillating.

A similar positive voltage channel is provided, comprising transformer 10-T2, diode bridge 10-DB2, capacitor 10-C2, the current limiting resistor 10-R2, the voltage regulator 10-VR2, potentiometer 10-R3, capacitor 10-C3, and diode 10-D2.

Integrated circuit 10-IC3 is a free-running astable multivibrator whose output drives transistor 10-Q1, to hold the drop counter circuit in the No-Drop alarm, non-alarmed state. Power for this oscillator is obtained on the regulator side of diode 10-D2; thus if the AC power to the battery charger is removed (as by a blown fuse, loose power cord, etc.) the No-Drop monitor alarm circuit will no longer be pulsed, and will alarm. Use of a discrete transistor 10-Q1 in the open collector mode insures low leakage during power failure, and eliminates the possibility of generating a spurious signal to the drop counter.

In many installations, it may be desirable to also incorporate with the hereinbefore described apparatus, an additional component forming drip rate setting apparatus designed to enable medical personnel to accurately set the rate at which fluids are infused into the patient by the IV set to reach a given volume in a given period of time, thus avoiding the necessity of maintaining a relatively constant vigil over the drop flow. By providing battery powered drop rate setter apparatus in conjunction with the drop monitoring apparatus which receives an electrical signal from the flow rate counter apparatus previously described and is provided with means for computing automatically the number of drops falling per second, the total ml's that will be infused in an hour at such drop rate, and the total ml's that would be infused in 8-hours at such drop rate, depending upon which readout format the nurse selects. Thus by reading only the display readout from this drop rate setter device, the operator may accurately adjust the rate of flow to correspond to the physician's orders, and carry out these procedures in a darkened room. Since the drop rate setter apparatus of the present invention is portable and hand-held, it is not necessary to have one device for each patient, and because of its size and format, which resembles a familiar hand-held calculator, it is readily adaptable for portable use by the nurse in many patients rooms.

As shown diagrammatically in FIGS. 11 and 12A, 12B and 12C, the drop rate setting device of the present invention includes an electronics package, indicated generally by the reference character 30, which is electrically connected to the battery and alarm box component 16 of the previously described embodiment by a 4-conductor electrical cable. This cable supplies both power and the drop signal to the drop rate setter electronics package 30. In the present embodiment, coming out of the package 30 is a 16-conductor ribbon cable indicated at 31 which connects to a hand-held portable calculator case 32 which houses the digital display, calculator electronics, reset switch, and ready to read light.

Figure 11:
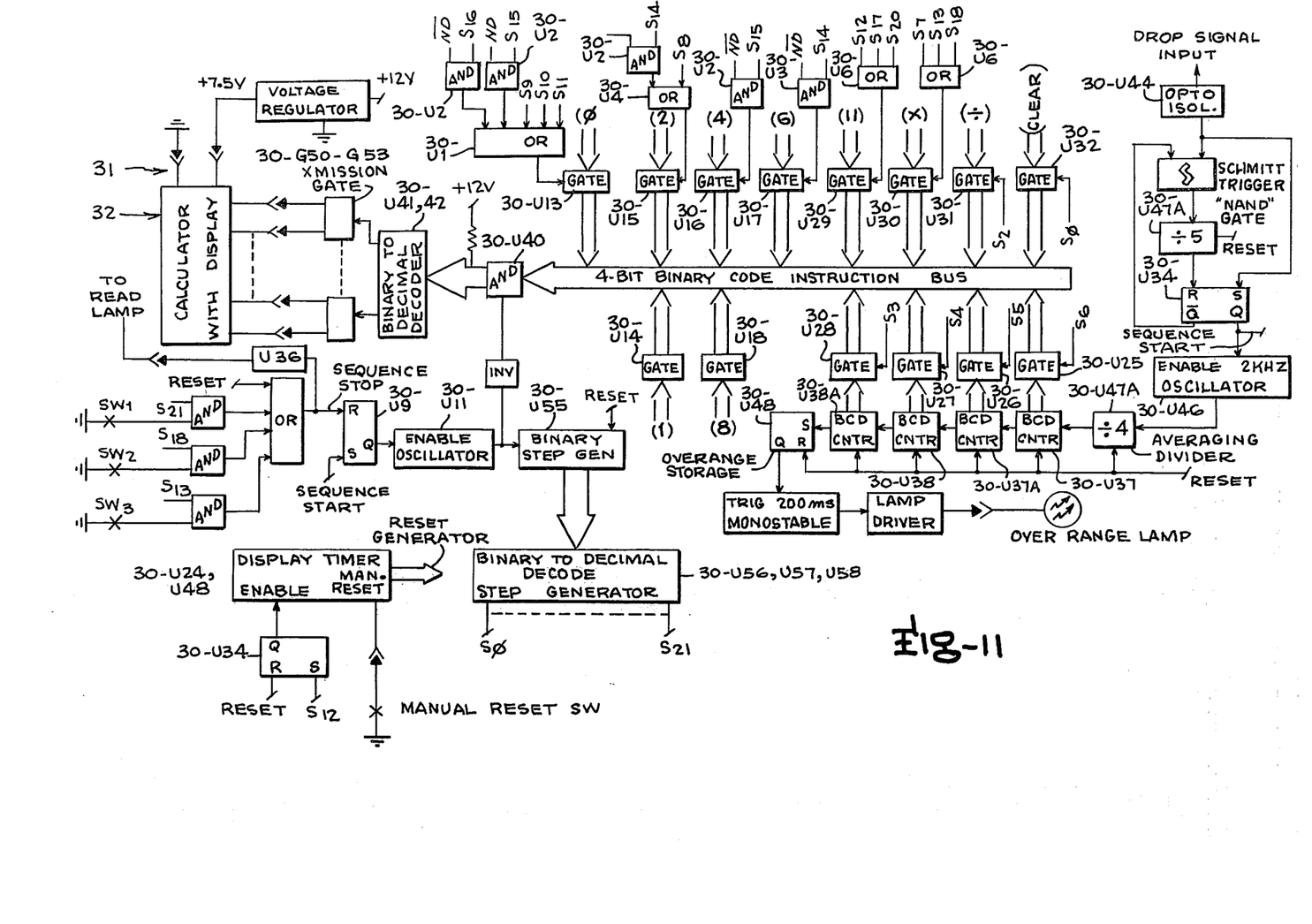
FIG. 11 is a block diagram of an operative embodiment of drop rate setting circuitry which may be used in an embodiment of the invention.
Figure 12:
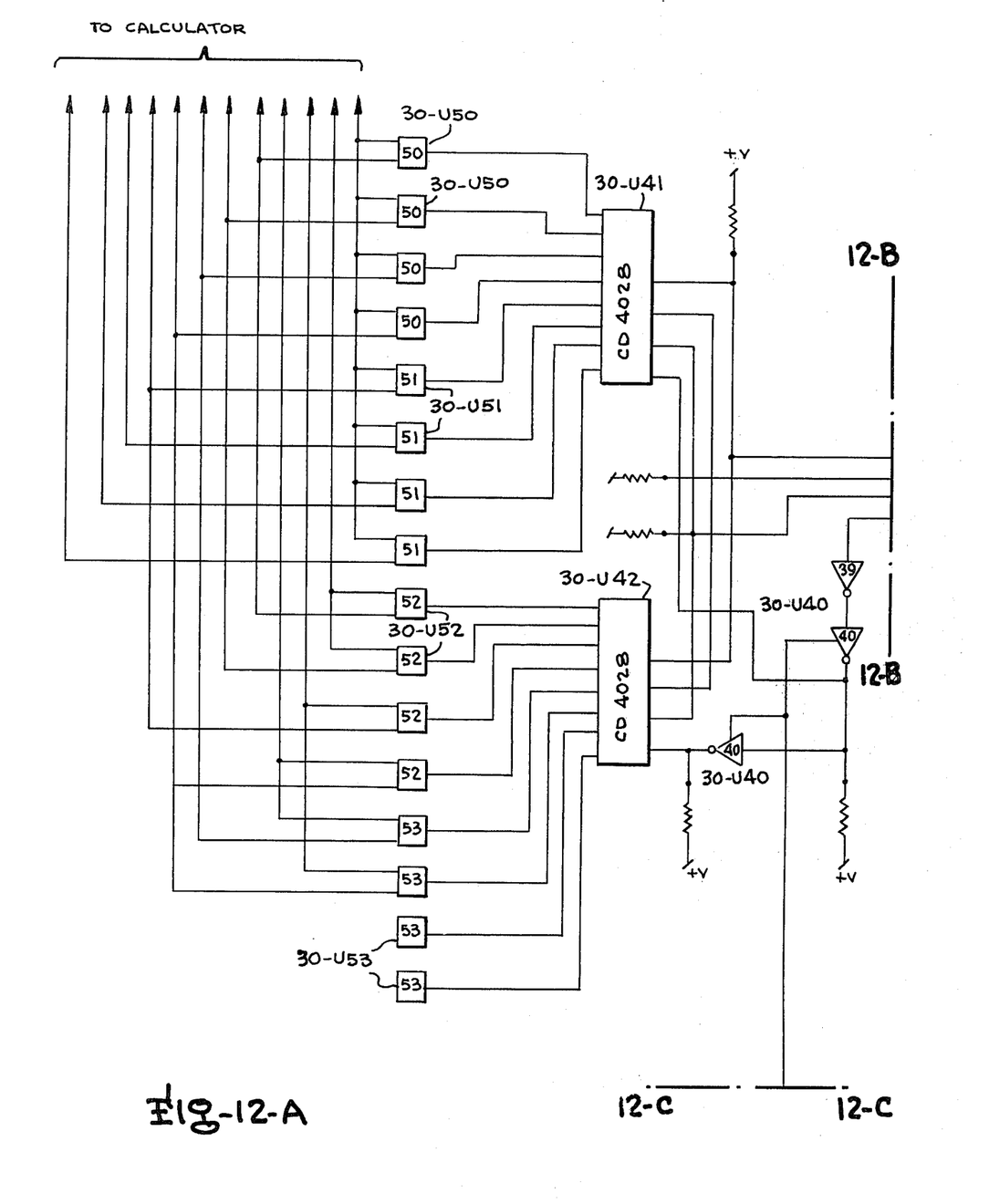

FIG. 11 is a block diagram of an example of the drop rate setting circuitry, and FIGS. 12A, 12B and 12C collectively provide a schematic diagram of the calculator controller section of the drop rate setter electronics package, wherein the symbols employed in FIGS. 11 and 12 indicated by customary symbolism commercially available, known electronic components making up the drop rate setter. Referring briefly to FIGS. 11 and 12, the 16-conductor ribbon cable 31 includes conductor connections from the display components of the calculator case 32 to the array of transmission gates indicated at 30-G50 to G53, formed for example from CD4016 quad bilateral switch integrated circuits. The outputs from these transmission gates function as keyboard switches. Outputs from the binary-to-decimal decoders 30-U41 and 30-U42 may be connected as indicated to CD4016 transmission gates indicated at 30-U13 to 30-U20 and 30-U25 to 30-U32 through a four bit binary code instruction bus. The 2 KHz oscillator, formed for example from a CD4047 multivibrator 30-U46 is connected to the divide-by-four averaging divider 30-U47 connected to oscillator count storage CD4518BE integrated circuits 30-U37 and U37A and 30-U38 and U38A as shown, and is also interconnected with divide-by-five averaging divider IC 30-U47A and NAND and NOR gate sections as indicated at 30-U34 and 30-U33 as shown.

Sections of integrated circuit 30-U40 functioning as an AND gate and connected with inverters are interconnected between decoder 30-U42 and the binary code instruction bus and connect to CD4520 binary step generators 30-U55 interconnected with binary-to-decimal decode step generator formed for example of CD4028AE decoders 30-U56, U57 and U58 as shown, enable oscillator 30-U11, for example a CD4047, is interconnected with the binary step generator and with the sequence start logic circuit 30-U9 and AND/OR gate sections of an IC such as a CD4086BE to provide a signal to trigger the monostable multivibrator 30-U36 (such as a CD4047) to provide a signal to the read lamp (LED) in the calculator case 32.

While the features and operation of the drip rate setting circuitry including the conventional calculator and the calculator controller section should be understandable to persons ordinarily skilled in the art from this description and the circuit diagrams and symbols herein provided, it will be apparent that other electronics may be provided to carry out the functions necessary for the drop rate setter, for example by programed microprocessors of COS/MOS technology now available.

Also it will be appreciated that the drop sensing head can be reduced in size and simplified by utilizing optical fiber cable for the conduction of the infrared light to the head as the emitter, and replacing the IR detector with a second optical fiber. For example, the dome lens of the IR light emitter 22-D4 may be ground off to within a few thousandths of an inch of the emitting chip, and a suitable optical fiber cut square and cemented to the face of the emitter chip. The optical fiber may be cut to a length approximating the electrical cords used for interconnection of the components in the previously described embodiment and provided with a dome lens of an empty IR emitter metal casing which can be inserted into the emitter cavity of the sensing head and secured in place. Similarly, the IR detector may be provided with an optical fiber of appropriate length cemented to the IR detector after its dome lens has been removed and provided with a dome lens on the other end of the optical fiber arranged in the same position and attitude as the IR detector of the previously described embodiment. Also, such optical fiber IR emitter and detector arrangements may be provided near the patient's bed to sense the drops descending through the drop chamber of the patient's IV assembly with the optical cables extending from the sensing location to a central monitoring point where the remainder of the electronics of the system are provided, thus permitting remote monitoring of the operation of the IV unit at the patient's bedside.

We claim:

1. Flow rate monitor for sensing and counting discrete liquid drops passing along a drop path through a drop sensing zone in an intravenous set drop chamber or the like and providing a count display, comprising detector means including a pulsed infrared radiation emitter and receiver pair forming an IR pulsed radiant energy monitoring beam located to be intercepted by said drop path at said sensing zone for interruption of the beam by said drops, the detector means including signal means responsive to drop interruption of said beam to produce a drop signal for each such drop interruption; said emitter and receiver comprising an emitter diode and a spectrally matched phototransistor and stabilization feedback circuit means coupled to said phototransistor including a transistor connected to said phototransistor providing a low impedance to the latter and connected to Operational Amplifiers interconnected to provide stabilization feedback voltage to said phototransistor to compensate for variations in gain of the emitter and receiver and maintain predetermined gain conditions on the phototransistor; electronic circuit means including counter means responsive to said drop signals for counting said drop signals and maintaining a totalized count of the number of drops since a selected start time to provide total drop count signals, first numeric display means responsive to said total drop count signals for presenting a visible numerical display continuously indicating the current drop count according to a predetermined numeric function, no-drop alarm means responsive to absence of said drop signals under predetermined criteria for producing a first sensible alarm condition signaling a no-drop condition, and checkpoint alarm means responsive to the total drop count reaching a prescribed total volume amount for producing a second identifiable alarm condition.

2. A flow rate monitor as defined in claim 1, wherein said pulse infrared radiation emitter and receiver pair are fixed in a sensor unit structure having means to releasably assemble the same around the drop sensing zone providing a beam sensing system of high immunity to ambient light and said drop indicator means including a visible light emitter carried by said sensor unit structure adjacent the drop sensing producing a light flash for each drop.

3. A flow rate monitor as defined in any of claims 1 or 2, wherein the detector means includes inhibit signal generating means for producing responsive to each drop signal an inhibit signal of selected time duration occupying a predetermined time period less than the operative between-drops-time-period to interrupt power consumption of the emitter during part of the interval between successive drops through the beam.

4. A flow rate monitor as defined in claim 2, including a second numeric display comprising checkpoint counter means and measns for adjusting such counter means to set the number readout of the second display to indicate selected checkpoint numbers signifying total volume of liquid to be passed along the drop path, and means coupling said checkpoint alarm means to said checkpoint counter means and the first-mentioned drop counter means to sense attainment of the checkpoint count by the drop counter means and activate said checkpoint alarm means to produce the second alarm signal.

5. A flow rate monitor as defined in claim 2, including a second numeric display located adjacent said first numeric display comprising checkpoint counter means and means for adjusting such counter means to set the number readout of the second display to indicate selected checkpoint numbers signifying total volume of liquid to be passed along the drop path, and means coupling said checkpoint alarm means to said checkpoint counter means and the first-mentioned drop counter means to sense attainment of the checkpoint count by the drop counter means and activate said checkpoint alarm means to produce the second alarm signal.

6. A flow rate monitor as defined in claim 2, wherein said electronic circuit means includes a battery forming the power supply for the electronic circuit means and for said detector means, battery monitoring circuit means responsive to the voltage level of the battery for producing a low-battery indicator signal when the battery voltage descends below a predetermined level, and alarm means responsive to said indicator signal to produce an audible alarm signifying the low-battery condition.

7. A flow rate monitor as defined in claim 2, including calculating means coupled to said electronic circuit means having means for accessing thereto drop information from said circuit means and means responsive thereto for calculating flow rate therefrom and translating the flow rate into various units of measure, said calculating means including means for displaying such calculation as a visible digital numeric display for use by attending personnel.

8. A flow rate monitor as defined in claim 2, including calculating means coupled to said electronic circuit means having means for accessing thereto drop information from said circuit means and means responsive thereto for calculating flow rate therefrom and translating the flow rate into various units of measure, said calculating means including a hand-held calculator having means for displaying such calculation as a visible digital numeric display for use by attending personnel.

9. A flow rate monitor as defined in claim 1, including a second numeric display comprising checkpoint counter means and means for adjusting such counter means to set the number readout of the second display to indicate selected checkpoint numbers signifying total volume of liquid to be passed along the drop path, and means coupling said checkpoint alarm means to said checkpoint counter means and the first-mentioned drop counter means to sense attainment of the checkpoint count by the drop counter means and activate said checkpoint alarm means to produce the second alarm signal.

10. A flow rate monitor as defined in claim 1, including a second numeric display located adjacent said first numeric display comprising checkpoint counter means and means for adjusting such counter means to set the number readout of the second display to indicate selected checkpoint numbers signifying total volume of liquid to be passed along the drop path, and means coupling said checkpoint alarm means to said checkpoint counter means and the first-mentioned drop counter means to sense attainment of the checkpoint count by the drop counter means and activate said checkpoint alarm means to produce the second alarm signal.

11. A flow rate monitor as defined in claim 1, wherein said electronic circuit means includes a battery forming the power supply for the electronic circuit means and for said detector means, battery monitoring circuit means responsive to the voltage level of the battery for producing a low-battery indicator signal when the battery voltage descends below a predetermined level, and alarm means responsive to said indicator signal to produce an audible alarm signifying the low-battery condition.

12. A flow rate monitor as defined in claim 1, including calculating means coupled to said electronic circuit means having means for accessing thereto drop information from said circuit means and means responsive thereto for calculating flow rate therefrom and translating the flow rate into various units of measure, said calculating means including means for displaying such calculation as a visible digital numeric display for use by attending personnel.

13. A flow rate monitor as defined in claim 1, including calculating means coupled to said electronic circuit means having means for accessing thereto drop information from said circuit means and means responsive thereto for calculating flow rate therefrom and translating the flow rate into various units of measure, said calculating means including a hand-held calculator having means for displaying such calculation as a visible digital numeric display for use by attending personnel.

14. A flow rate monitor for sensing and counting discrete liquid drops passing along a drop path through a drop sensing zone as an intravenous set drop chamber or the like and providing a count display, comprising detector means including a pulsed infrared radiation emitter and receiver pair forming a IR pulsed radiant energy monitoring beam located to be intercepted by said drop path at said sensing zone for interruption of the beam by aaid drops, the detector means including signal means responsive to drop interruption of said beam to produce a drop signal for each such drop interruption; electronic circuit means including counter means responsive to said drop signals for counting said drop signals and maintaining a totalized count of the number of drops since a selected start time to provide total drop count signals, first numeric display means responsive to said total drop count signals for presenting a visible numerical display continuously indicating the current drop count according to a predetermined numeric function, no-drop alarm means responsive to absence of said drop signals under predetermined criteria for producing a first sensible alarm condition signaling a no-drop condition, and checkpoint alarm means responsive to the total drop count reaching a prescribed total volume amount for producing a second identifiable alarm condition; said detector means including inhibit signal generating means for producing responsive to each drop signal an inhibit signal of selected time duration occupying a predetermined time period less than the operative between-drops-time-period to interrupt power consumption of the emitter during part of the interval between successive drops through the beam.

15. A flow rate monitor as defined in claim 14, including a second numeric display comprising checkpoint counter means and means for adjusting such counter means to set the number readout of the second display to indicate selected checkpoint numbers signifying total volume of liquid to be passed along the drop path, and means coupling said checkpoint alarm means to said checkpoint counter means and the first-mentioned drop counter means to sense attainment of the checkpoint count by the drop counter means and activate said checkpoint alarm means to produce the second alarm signal.

16. A flow rate monitor as defined in claim 14, including a second numeric display located adjacent said first numeric display comprising checkpoint counter means and means for adjusting such counter means to set the number readout of the second display to indicate selected checkpoint numbers signifying total volume of liquid to be passed along the drop path, and means coupling said checkpoint alarm means to said checkpoint counter means and the first-mentioned drop counter means to sense attainment of the checkpoint count by the drop counter means and activate said checkpoint alarm means to produce the second alarm signal.

17. A flow rate monitor as defined in claim 14, wherein said electronic circuit means includes a battery forming the power supply for the electronic circuit means and for said detector means, battery monitoring circuit means responsive to the voltage level of the battery for producing a low-battery indicator signal when the battery voltage descends below a predetermined level, and alarm means responsive to said indicator signal to produce an audible alarm signifying the low-battery condition.

18. A flow rate monitor as defined in claim 14, including calculating means coupled to said electronic circuit means having means for accessing thereto drop information from said circuit means and means responsive thereto for calculating flow rate therefrom and translating the flow rate into various units of measure, said calculating means including means a hand-held calculator having for displaying such calculation as a visible digital numeric display for use by attending personnel.

* * * * *